(12) United States Patent
Fujii

(10) Patent No.: US 7,192,727 B2
(45) Date of Patent: Mar. 20, 2007

(54) REAGENT FOR MEASURING ALANINE AMINOTRANSFERASE ACTIVITY

(75) Inventor: Takayuki Fujii, Tokyo (JP)

(73) Assignee: Mitsubishi Kagaku Iatron, Inc., Tokyo (JP)

( * ) Notice: Subject to any disclaimer, the term of this patent is extended or adjusted under 35 U.S.C. 154(b) by 0 days.

(21) Appl. No.: 10/507,105

(22) PCT Filed: Mar. 12, 2003

(86) PCT No.: PCT/JP03/02897

§ 371 (c)(1),
(2), (4) Date: Sep. 10, 2004

(87) PCT Pub. No.: WO03/076652

PCT Pub. Date: Sep. 18, 2003

(65) Prior Publication Data

US 2005/0221416 A1    Oct. 6, 2005

(30) Foreign Application Priority Data

Mar. 12, 2002 (JP) ............................ 2002-066814

(51) Int. Cl.
*C12Q 1/52* (2006.01)
*C12Q 1/32* (2006.01)

(52) U.S. Cl. .......................... 435/16; 435/26
(58) Field of Classification Search ............ 435/16, 435/26, 22, 25, 810
See application file for complete search history.

(56) References Cited

U.S. PATENT DOCUMENTS 4,241,179 A * 12/1980 Madappally et al. ......... 435/16
5,589,348 A   12/1996 Kaufman et al.

FOREIGN PATENT DOCUMENTS

| EP | 0 133 064 A1 | 2/1985 |
| EP | 1 083 235 A2 | 3/2001 |
| EP | 1083235 A | 3/2001 |
| JP | 9-070299 A | 3/1997 |

* cited by examiner

*Primary Examiner*—Jon Weber
*Assistant Examiner*—Paul C. Martin
(74) *Attorney, Agent, or Firm*—Sughrue Mion, PLLC

(57) ABSTRACT

A reagent for measuring an alanine aminotransferase activity comprising L-alanine, 2-oxoglutaric acid, lactate dehydrogenase, and reduced nicotinamide adenine dinucleotide, characterized by further comprising a substance having an activity of inhibiting lactate dehydrogenase activity is disclosed. Further, a method for measuring an alanine aminotransferase activity, characterized by bringing a sample to be analyzed, which may contain alanine aminotransferase, into contact with L-alanine, 2-oxoglutaric acid, lactate dehydrogenase, reduced nicotinamide adenine dinucleotide, and a substance having an activity of inhibiting a lactate dehydrogenase activity is disclosed. According to the reagent and method, an increase in the reagent blank reaction, i.e., an increase in the initial absorbance, can be suppressed.

4 Claims, 2 Drawing Sheets

REAGENT FOR MEASURING ALANINE AMINOTRANSFERASE ACTIVITY

This application is a 371 of PCT/JP03/02897 filed Mar. 12,2003.

TECHNICAL FIELD

The present invention relates to a reagent for measuring an alanine aminotransferase activity.

BACKGROUND ART

Alanine aminotransferase (hereinafter referred to as ALT) is an enzyme abundantly distributed in the heart or liver. Because ALT is released to blood during a disease, the measurement of an ALT activity in a body fluid such as urine or blood is important as a marker for a diagnosis of a heart or liver disease or observation after treatment thereof.

In a method commonly used for measuring the ALT activity, pyruvic acid, which is generated from L-alanine and 2-oxoglutaric acid as substrates by ALT, is changed to lactic acid by lactate dehydrogenase (hereinafter referred to as LD), and a decreased amount of reduced nicotinamide adenine dinucleotide (hereinafter referred to as NADH) coexisting is measured at the wavelength of approximately 340 nm.

The reaction formulae are as follows:

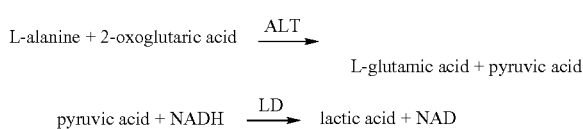

In the above formula, NAD means oxidized nicotinamide adenine dinucleotide.

As previously described, the measurement of ALT activity is important as a marker for a diagnosis of a heart or liver disease or observation after treatment thereof, and is carried out internationally. However, because various methods for measuring the ALT activity are known and used, different values obtained in accordance with different facilities or persons lack compatibility, and thus there is concern that problems in clinical diagnosis may arise. Therefore, recommendations in which reaction principles, the composition of reagents, concentrations of reagents, and the like are prescribed are suggested in each country, and the ALT activity is thus measured in each facility, to ensure compatibility with values measured in accordance with the recommendations.

In Japan, the Japan Society of Clinical Chemistry (JSCC) published in 1989 a recommendation for measuring the ALT activity [JSCC: Recommendation for measuring enzyme activities in human serum-alanine aminotransferase-(1989-08-30), Japanese Journal of Clinical Chemistry, 18(4), 250–262 (1989)].

The recommendation published by JSCC is a method in which common enzyme activities are measured under optimal conditions, which may be shared by technical levels in a clinical laboratory or the like, to ensure the compatibility of measuring values, and thus it cannot be generally used as a daily test. Therefore, manufacturers of reagents for clinical laboratory test supply reagents capable of ensuring compatibility between measuring values and the JSCC recommendation, and have conducted intensive studies into the provision of stable and low-cost reagents to obtain accurate and precise measuring values and the compatibility between measuring values and the JSCC recommendation.

In facilities such as a clinical laboratory where the ALT activity is measured, reagents for measuring the ALT activity, which are supplied by the manufacturers of reagents for clinical laboratory test and ensure the compatibility between measuring values and the JSCC recommendation, are generally used as a daily test. However, because samples from a living body are mixtures of various components and reagents for measuring the ALT activity are also mixtures of various components, it is very difficult to develop a reagent which is stable and not affected by impurities, for measuring the ALT activity.

Particularly, in an automatic analyzer in which only the setting of measuring reagents and the setting of measuring conditions are needed, measurement is often carried out after keeping reagents open for several weeks. In this case, the reagents for measuring the ALT activity absorb carbon dioxide in air, and then pH in the reagents followed by the reagent blank reaction changes, to produce a problem, i.e., errors in the measuring values of ALT activity obtained.

Therefore, the object of the present invention is to provide a reagent for measuring the ALT activity which can suppress an increase in the reagent blank reaction, i.e., an increase in the initial absorbance.

DISCLOSURE OF THE INVENTION

The object can be solved by the present invention, i.e., a reagent for measuring an alanine aminotransferase activity comprising L-alanine, 2-oxoglutaric acid, lactate dehydrogenase, and reduced nicotinamide adenine dinucleotide, characterized by further comprising a substance having an activity of inhibiting a lactate dehydrogenase activity.

According to a preferred embodiment of the present invention, the reagent for measuring an alanine aminotransferase activity is a two reagent-components system, and contains the substance having an activity of inhibiting a lactate dehydrogenase activity in either of a first reagent-component or a second reagent-component or both of the first and second reagent-components.

According to another preferred embodiment of the present invention, the reagent for measuring an alanine aminotransferase activity is a two reagent-components system, and contains lactate dehydrogenase and the substance having an activity of inhibiting a lactate dehydrogenase activity in the same reagent-component.

According to still another preferred embodiment of the present invention, the reagent for measuring an alanine aminotransferase activity is a two reagent-components system, and contains at least lactate dehydrogenase in a first reagent-component and at least 2-oxoglutaric acid in a second reagent-component.

According to still another preferred embodiment of the present invention, the substance having an activity of inhibiting a lactate dehydrogenase activity is oxamic acid or a salt thereof.

Further, the present invention relates to a method for measuring an alanine aminotransferase activity, characterized by bringing a sample to be analyzed, which may contain alanine aminotransferase, into contact with L-alanine, 2-oxoglutaric acid, lactate dehydrogenase, reduced nicotinamide adenine dinucleotide, and a substance having an activity of inhibiting a lactate dehydrogenase activity.

Furthermore, the present invention relates to a method for measuring an alanine aminotransferase activity, characterized by comprising the steps of:

bringing a sample to be analyzed, which may contain alanine aminotransferase, into contact with L-alanine, 2-oxoglutaric acid, lactate dehydrogenase, reduced nicotinamide adenine dinucleotide, and a substance having an activity of inhibiting a lactate dehydrogenase activity, and measuring a decreased amount of reduced nicotinamide adenine dinucleotide or an increased amount of oxidized nicotinamide adenine dinucleotide generated.

According to a preferred embodiment of the measuring method of the present invention, the substance having an activity of inhibiting a lactate dehydrogenase activity is oxamic acid or a salt thereof.

According to another preferred embodiment of the measuring method of the present invention, a concentration of oxamic acid or a salt thereof is 0.005 to 5 mmol/L as a final concentration in a measuring system.

According to still another preferred embodiment of the measuring method of the present invention, a concentration of lactate dehydrogenase is 100 U/L or more as a final concentration in a measuring system.

BEST MODE FOR CARRYING OUT THE INVENTION

Figure 1:
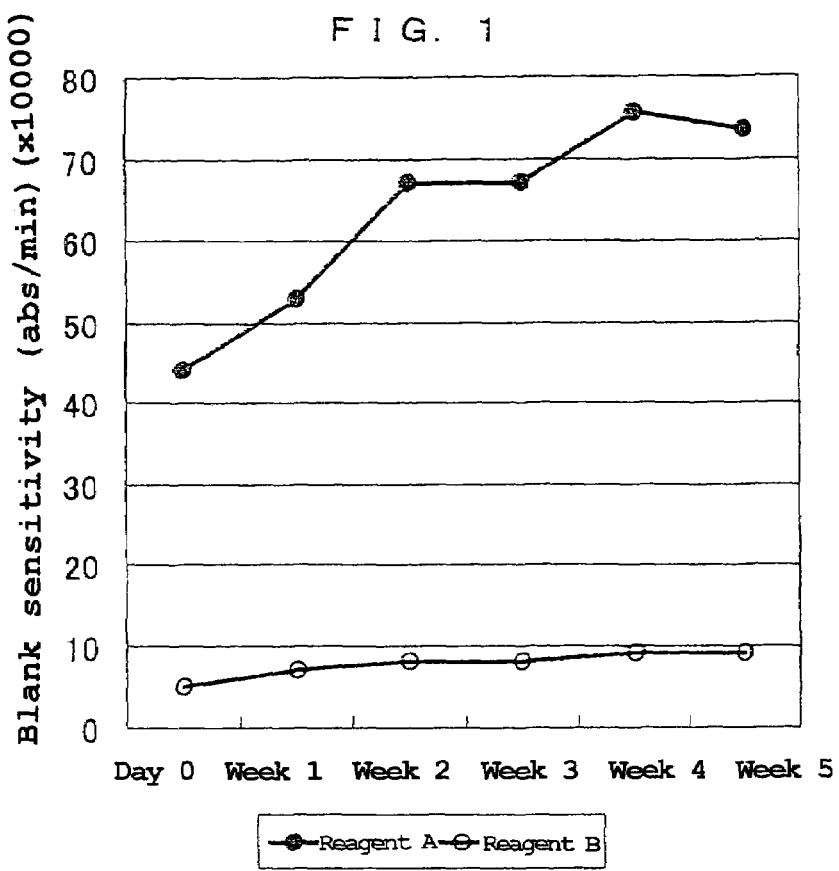
FIG. 1 a graph showing a time course for a blank sensitivity in the reagents for measuring an ALT activity of the present invention and for comparison.

The reagent of the present invention for measuring an ALT activity is an improved reagent of a known reagent for measuring an ALT activity comprising L-alanine, 2-oxoglutaric acid, LD, and NADH. In the reagent for measuring an ALT activity comprising L-alanine, 2-oxoglutaric acid, LD, and NADH, pyruvic acid, which is generated from L-alanine and 2-oxoglutaric acid as substrates by ALT, is changed to lactic acid by LD, and a decreased amount of NADH coexisting or an increased amount of NAD generated is measured at the wavelength of approximately 340 nm.

The reagent for measuring an ALT activity of the present invention comprises a substance having an activity of inhibiting an LD activity (hereinafter referred to as an LD inhibitor) in addition to the known components. The LD inhibitor used in the present invention is not particularly limited, but there may be mentioned, for example, oxamic acid, oxalic acid, oxalacetic acid, pyruvic acid, phosphoenolpyruvic acid, sodium dodecyl sulfate, lactic acid, or hydroxyglutaric acid, or salts thereof. Oxamic acid or a salt thereof such as sodium salt, potassium salt, or lithium salt, usually does not lead to errors in measuring an ALT activity, and thus is preferable.

A concentration of the LD inhibitor contained in the reagent for measuring an ALT activity of the present invention may be changed in accordance with the kind of the LD inhibitor used, and thus is not particularly limited, so long as it is the concentration exhibiting the LD activity which does not affect a reagent for measuring an ALT activity. The final concentration in a measuring system may be generally 0.001 to 100 mmol/L, obtained by adjusting the concentration contained in the measuring reagent.

The term "exhibiting the LD activity which does not affect a reagent for measuring an ALT activity" as used herein means that at least an LD activity capable of measuring the ALT activity remains in a sample to be analyzed. Even if the LD activity is inhibited by the LD inhibitor, such a reagent for measuring an ALT activity can be used, so long as a minimum LD activity enough for measurement remains. In addition, the object of the present invention is to suppress the reagent blank reaction, and thus appropriate amounts of LD and the LD inhibitor can be selected, so as to exhibit the LD activity which does not affect a reagent for measuring an ALT activity and to reduce the reagent blank reaction to as low as possible.

More particularly, for example, when oxamic acid is used as the LD inhibitor, the desired effect can be obtained by adding oxamic acid so that the final concentration in the measuring system becomes preferably 0.005 to 5 mmol/L, more preferably 0.02 to 1 mmol/L. As described below, when the reagent components are divided into the first reagent-component and the second reagent-component, the same effect can be obtained by adding oxamic acid to either of the first reagent-component or the second reagent-component or both of the first and second reagent-components, so long as the final concentration is within the above range. Further, when the LD inhibitor coexists with LD, LD can be stabilized.

Among the components contained in the reagent for measuring an ALT activity of the present invention, each component contained in known reagents for measuring an ALT activity, i.e., LD, NADH, L-alanine, and 2-oxoglutaric acid, can be used in a manner similar to that of known reagents.

For example, a naturally occurring LD, such as that derived from chicken heart, pig heart, pig muscle, or Leuconostoc mesenteroides, or a recombinant LD thereof, can be used as LD. Therefore, the origin thereof is not particularly limited.

The concentration of LD contained in the reagent for measuring an ALT activity of the present invention can be appropriately selected so that the final concentration in a measuring system becomes at least 100 U/L or more. In this connection, the reagent for measuring an ALT activity of the present invention is characterized by further comprising the LD inhibitor, and thus the concentration can be appropriately selected so that the final concentration of the LD activity becomes at least 100 U/L or more in consideration of the LD inhibition by the LD inhibitor. For example, when oxamic acid as the LD inhibitor is added, so that the concentration becomes 0.02 to 1 mmol/L, an appropriate amount of LD can be used so that the final concentration of the LD activity becomes at least 100 U/L or more.

The term "LD activity" as used herein means an activity of reducing pyruvic acid to lactic acid. The unit "U" is defined as the amount of enzyme activity obtained when converting 1 μmol of the substrate (pyruvic acid) to the product (lactic acid) for a minute (standard temperature 30° C.).

The concentration of NADH contained in the reagent for measuring an ALT activity of the present invention may be preferably 0.05 to 2 mmol/L, more preferably 0.1 to 0.5 mmol/L, as the final concentration in a measuring system.

The concentration of L-alanine as one of the substrates may be preferably 100 to 3000 mmol/L, more preferably 200 to 2000 mmol/L, as the final concentration in a measuring system.

The concentration of 2-oxoglutaric acid as another substrate may be preferably 1 to 500 mmol/L, more preferably 5 to 100 mmol/L, as the final concentration in a measuring system.

The reagent for measuring an ALT activity of the present invention may contain an appropriate buffer, as known reagents for measuring an ALT activity of the present invention. The buffer used may be a buffer which does not cause an adverse effect when measuring the ALT activity and can be appropriately selected from known buffers. There may be mentioned, for example, tris(hydroxymethyl)aminomethane, phosphoric acid, 2-[4-(2-hydroxyethyl)-1-piperazyl]ethanesulfonic acid, bis(2-hydroxymethyl)iminotris(hydroxyethyl)methane, 2-hydroxy-N-tris(hydroxymethyl)methyl-3-aminopropanesulfonic acid, N-tris(hydroxymethyl)methyl-2-aminoethanesulfonic acid, or n-ethylmorpholine.

The reagent for measuring an ALT activity of the present invention may optionally contain, in addition to the essential components and the buffer, commonly used components such as chelating agents [for example, ethylenediaminetetraacetic acid (EDTA)], preservatives (for example, azide), stabilizers (for example, albumin or glycerol), and/or detergents.

The combination of reagent components in the reagent for measuring an ALT activity of the present invention is not particularly limited, as known reagents for measuring an ALT activity, and may be a one reagent-component system or a two reagent-components system. Generally, a reagent in which the components are divided into stable conditions and reactions can be carried out under optimal conditions for measuring the activity is preferred. In such a combination, for example, the first reagent-component containing NADH, LD, and the like, which are stable under alkaline conditions, and the second reagent-component containing 2-oxoglutaric acid and the like are prepared, so that the concentrations thereof and pH become optimum for measuring the activity during reactions, and the LD inhibitor and 1-alanine can be added to either of the first reagent-component or the second reagent-component or both of the first and second reagent-components. However, the present invention is not particularly limited to these combinations.

When measuring a sample to be analyzed, which may contain pyruvic acid, for example, a body fluid (such as blood, serum, plasma, or urine), cells, or tissues, a two reagent-components system in which at least LD is contained in the first reagent-component and 2-oxoglutaric acid is contained in the second reagent-component is preferable, to remove effects due to pyruvic acid derived from the sample. The ALT activity can be measured without effects due to pyruvic acid derived from the sample, by mixing the sample which may contain pyruvic acid with the first reagent-component containing LD to eliminate pyruvic acid derived from the sample, and adding the second reagent-component thereto.

In this connection, in the case of a two reagent-components system in which at least LD and 2-oxoglutaric acid are contained in the second reagent-component, the ALT activity can be measured by adding the second reagent-component and incubating for a member of seconds to approximately a minute to eliminate pyruvic acid derived from the sample. Alternatively, in the case of a one reagent-component system, the ALT activity can be measured. Therefore, the reagent for measuring an ALT activity of the present invention is not limited to the specific combinations of reagent components.

The reagent of the present invention for measuring an ALT activity can be used, for example, in the method of the present invention for measuring an ALT activity. In the method of the present invention for measuring an ALT activity, the ALT activity can be measured by bringing a sample to be analyzed into contact with L-alanine, 2-oxoglutaric acid, LD, NADH, and an LD inhibitor, and measuring a decreased amount of NADH or an increased amount of NAD generated at the wavelength of approximately 340 nm.

The sample to be analyzed is not particularly limited, so long as it is a sample which may contain the ALT activity. There may be mentioned, for example, body fluids commonly used in clinical diagnosis (such as blood, serum, plasma, or urine), cells, tissues, or experimental samples.

Mechanisms

The present inventor considers the reason for the suppressing of the reagent blank reaction in the reagent for measuring an ALT activity of the present invention, as follows. However, the present invention is not limited to the following hypothesis.

It is known that LD contained in the reagent for measuring an ALT activity of the present invention has not only a dehydrogenase activity to lactic acid as a major enzyme activity, but also an activity of reducing 2-oxoglutaric acid, i.e., a 2-hydroxyglutaric acid dehydrogenase (HGD) activity [Japanese Journal of Clinical Chemistry, 18(4), 250–262 (1989)]. The reaction is as follows:

2-oxoglutaric acid + NADH $\xrightarrow{HGD}$ 2-hydroxyglutaric acid + NAD

As previously described in BACKGROUND ART, in widely used methods for measuring the ALT activity, including the recommendation published by the Japan Society of Clinical Chemistry, 2-oxoglutaric acid is used as a substrate. Therefore, when LD has the dehydrogenase activity to 2-oxoglutaric acid (i.e., HGD activity), NADH is oxidized, and the reagent blank and the reagent blank reaction are increased.

Further, the dehydrogenase activity to 2-oxoglutaric acid is changed by a pH change, to generate errors in the obtained measuring values of the ALT activity. For example, in an automatic analyzer in which only the setting of measuring reagents and the setting of measuring conditions are needed, measurement is often carried out after keeping reagents open for several weeks. In this case, the reagents for measuring the ALT activity absorb carbon dioxide in air, and then pH in the reagents followed by the reagent blank reaction changes, to generate errors in the obtained measuring values of the ALT activity.

Furthermore, the dehydrogenase activity to 2-oxoglutaric acid produces a problem in that an apparent Km of LD to pyruvic acid is increased during a measuring of the ALT activity, to cause negative errors in the measured values of the activity. It is considered that the reagent blank reaction is a reaction in which 2-oxoglutaric acid is reduced by LD per se, i.e., the HGD activity.

The present inventor confirmed that LD exhibits the HGD activity and that the reagent blank is changed in accordance with an amount of LD added in the reagent for measuring an ALT activity. Further, the optimum pH of the HGD activity is between a weak acidity and around neutral. For example, when an amount of LD is increased, the reagent blank is increased. In addition, when measuring the ALT activity under weak alkaline conditions, the reagent blank is increased and accurate measured values of the ALT activity cannot be obtained, due to a decreased pH of reagents due to keeping the reagents open.

It is considered that the reagent blank can be reduced by decreasing an amount of LD. However, if the amount of LD is too small, an amount of LD required to measure the ALT activity is insufficient, and thus a quantitativeness cannot be obtained. Further, an increased reagent blank due to a decreased pH of reagents caused by keeping reagents open can be avoided by changing the pH during the measuring of the ALT activity to alkaline conditions. However, this is not appropriate, because the optimum pH of the ALT activity is a weak alkaline.

An inhibitor of the HGD activity has not been known until now, and under these circumstances, the present inventor considered the following. That is, an LD inhibitor is added to a known reagent for measuring an ALT activity, to inhibit the HGD activity of LD per se and, as a result, to reduce the reagent blank without the loss of quantitativeness. Further, an increased reagent blank due to a decreased pH of reagents caused by keeping reagents open can be avoided, and negative errors in measured values of the ALT activity due to an increased apparent Km of LD to pyruvic acid can be reduced.

EXAMPLES

The present invention now will be further illustrated by, but is by no means limited to, the following Examples.

Preparative Example 1

As the reagent for measuring an ALT activity of the present invention, a two reagent-components system composed of the first reagent-component containing the components shown in Table 1 and the second reagent-component containing the components shown in Table 2 was prepared.

Further, as a known reagent for measuring an ALT activity for comparison, a two reagent-components system, which was the same as that of the reagent of the present invention except that oxamic acid was not contained in the first reagent-component, was prepared.

Hereinafter, the two reagent-components system for comparison is referred to as "reagent A" and the two reagent-components system of the present invention is referred to as "reagent B". The prepared reagents A and B were transferred to sealed containers and kept therein until used in the following Example for evaluation.

TABLE 1

| Concentration | Components |
|---|---|
| 20 mmol/L | Tris-HCl (pH 9.20) |
| 200 mmol/L | L-alanine |
| 0.5 mmol/L | oxamic acid |
| 0.095% | sodium azide |
| 0.25 mol/L | NADH |
| 3 KU/L | LD (recombinant LD; Oriental Yeast Co., Ltd.) |

TABLE 2

| Concentration | Components |
|---|---|
| 360 mmol/L | Tris-HCl (pH 4.50) |
| 1080 mmol/L | L-alanine |
| 63 mmol/L | 2-oxoglutaric acid |
| 0.01% | EDTA2Na |

Example for Evaluation 1: Evaluation of Reagent for Measuring an ALT Activity of the Present Invention (1) Measurement of Reagent Blank Reagent containers for an automatic analyzer (7170S; Hitachi Ltd.) were filled with the first reagent-component (60 mL) and the second reagent-component (20 mL) of the reagent A for comparison, and the first reagent-component (60 mL) and the second reagent-component (20 mL) of the reagent B of the present invention prepared in Preparative Example 1, respectively. The reagent containers were set in the automatic analyzer and allowed to stand for 5 weeks. The automatic analyzer used in the evaluation had a cooling unit and the reagent containers were kept at approximately 10° C. The reagent containers were kept open.

Immediately after the standing, and after 1 week, 2 weeks, 3 weeks, 4 weeks, and 5 weeks, each reagent blank of the reagents A and B was measured in accordance with the following procedure.

More particularly, to each reaction cell in the automatic analyzer, 7.5 µL of physiological saline as a sample followed by 150 µL of the first reagent-component were added, stirred, and incubated at 37° C. for 5 minutes, and then 50 µL of the second reagent-component was further added, stirred, and incubated at 37° C. for 5 minutes. After approximately 1 minute to 5 minutes (i.e., for 4 minutes) from the addition of the second reagent-component, an amount of change in absorbance at the wavelength of 340 nm was measured, and an amount of change in absorbance per minute was calculated as a blank sensitivity. The results are shown in FIG. 1.

As shown in FIG. 1, during the keeping of the reagent containers open, the reagent blank in the reagent A for comparison was increased with time, while that in the reagent B of the present invention showed little change.

(2) Measurement of ALT Activity in Pooled Serum

As similar to the above Example for evaluation 1(1), the reagents A and B were allowed to stand for 5 weeks. Immediately after the standing, and after 1 week, 2 weeks, 3 weeks, 4 weeks, and 5 weeks, the ALT activity in a sample (a pooled serum) was measured in accordance with the following procedure.

More particularly, 7.5 µL of a pooled serum or physiological saline (reagent blank) followed by 150 µL of the first reagent-component were added, stirred, and incubated at 37° C. for 5 minutes, and then 50 µL of the second reagent-component was further added, stirred, and incubated at 37° C. for 5 minutes. After approximately 1 minute to 5 minutes (i.e., for 4 minutes) from the addition of the second reagent-component, an amount of change in absorbance at the wavelength of 340 nm was measured, and an amount of change in absorbance per minute was calculated. The ALT activity was calibrated on the basis of measured values using an enzyme calibrator (INTERNATIONAL REAGENTS CORPORATION) instead of the pooled serum.

Figure 2:
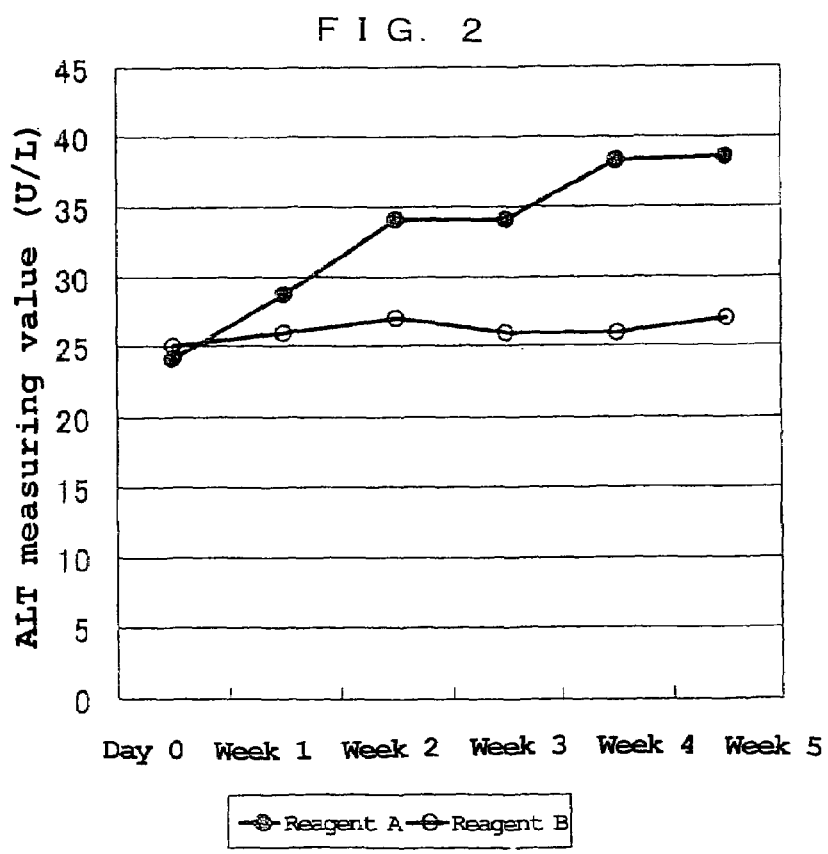
FIG. 2 is a graph showing a time course for the ALT activity in a pooled serum measured using the reagents for measuring an ALT activity of the present invention and for comparison.

The results are shown in FIG. 2. As shown in FIG. 2, with respect to measured values of the pooled serum, the measured values of the ALT activity in the reagent A for comparison were increased with time, while those in the reagent B of the present invention showed little change, during the keeping of the reagent containers open.

Example for Evaluation 2: Evaluation of LD Stability in Reagent for Measuring an ALT Activity of the Present Invention In the present example for evaluation, a time course for a residual ratio of the LD activity in each first reagent-component was examined by the following procedure. That is, 60 mL of the first reagent-component of the reagent A for comparison and 60 mL of the first reagent-component of the reagent B of the present invention prepared in Preparative Example 1 were transferred to 70 mL-volume polyethylene bottles with caps, respectively. After the closed bottles were incubated at 25° C. or 37° C. for 3 weeks, a time course was examined.

More particularly, immediately after the incubation, and after 1 week, 2 weeks, and 3 weeks, each reagent was collected. For measurement, each reagent was diluted to $1/10$ with 50 mmol/L phosphate buffer (pH 7.50) containing 0.1% bovine serum albumin as a sample, and measured using an automatic analyzer (7170S; Hitachi Ltd.) in accordance with the following procedure.

To 7.5 µL of each sample, 150 µL of reagent 1 for measuring an LD activity [50 mmol/L phosphate buffer (pH 7.50) and 0.25 mmol/L NADH] was added and incubated at 37° C. for 5 minutes, and then 30 µL of reagent 2 for measuring an LD activity [50 mmol/L phosphate buffer (pH 7.50) and 12 mmol/L lithium salt of pyruvic acid] was further added, stirred, and incubated at 37° C. for 5 minutes. After approximately 1 minute to 2 minutes from the addition of the reagent 2 for measuring an LD activity, an amount of change in absorbance per minute at the wavelength of 340 nm was measured. Each residual ratio of the LD activity was calculated when the amount of change in absorbance at the first day of incubation was regarded as 100%.

Figure 3:
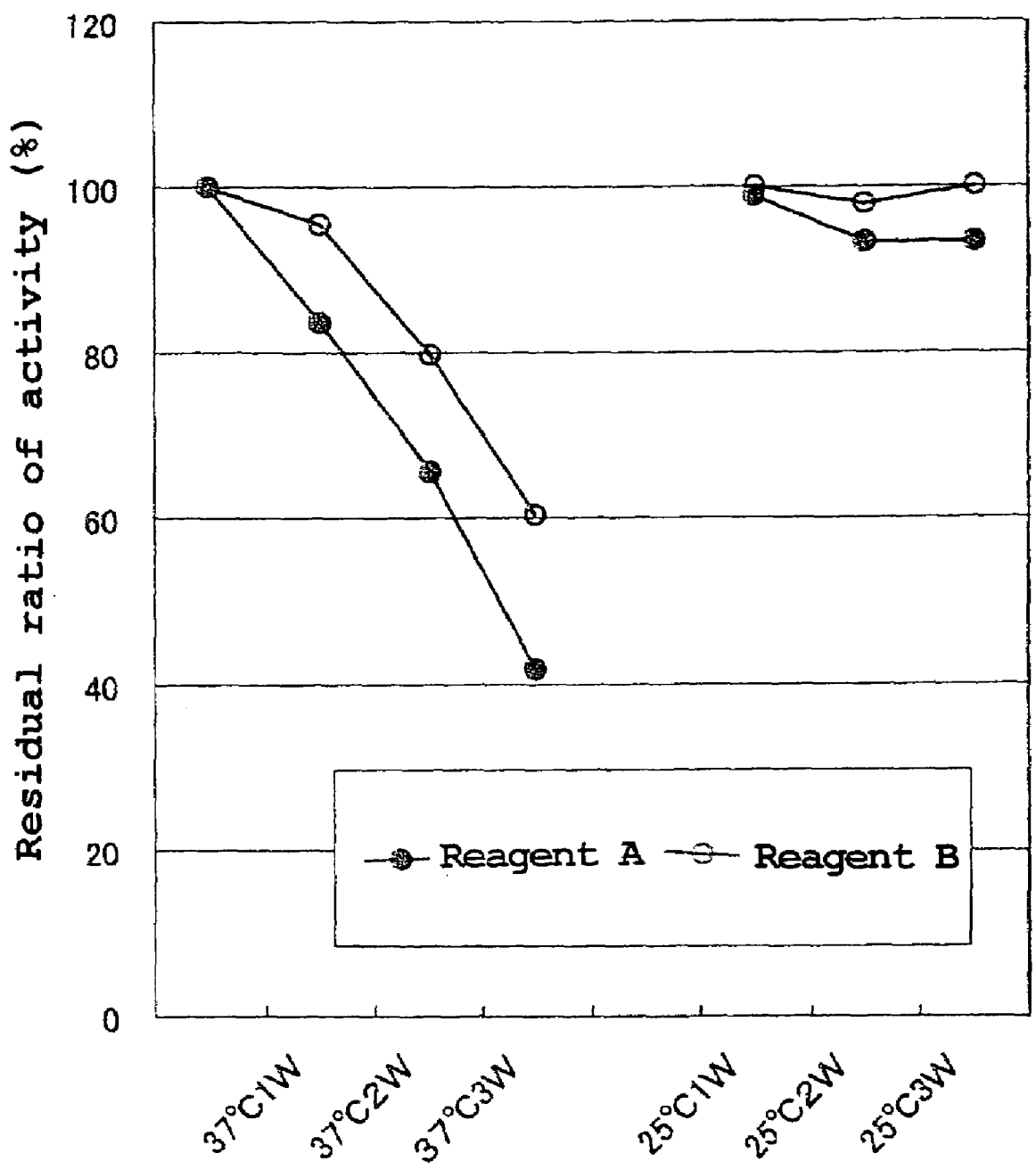
FIG. 3 is a graph showing an LD stability of the reagents for measuring an ALT activity of the present invention and for comparison.

The results are shown in FIG. 3. In FIG. 3, the terms "1W", "2W", and "3W" mean the results after 1 week, 2 weeks, and 3 weeks from the beginning of the incubation, respectively.

As shown in FIG. 3, the residual ratio of the LD activity in the reagent B of the present invention was higher than that in the reagent A for comparison, both at 37° C. and at 25° C.

INDUSTRIAL APPLICABILITY

According to the reagent for measuring an ALT activity of the present invention, an increased reagent blank reaction, i.e., an increased initial absorbance, can be suppressed, and thus accurate measured values of the ALT activity can be obtained. Further, the reagent of the present invention exhibits an activity of stabilizing LD.

Although the present invention has been described with reference to specific embodiments, various changes and modifications obvious to those skilled in the art are possible without departing from the scope of the appended claims.

The invention claimed is:

1. In a method for measuring an alanine aminotransferase activity in a sample, said method comprising the steps of: bringing the sample into contact with L-alanine, 2-oxoglutaric acid, lactate dehydrogenase, and reduced nicotinamide adenine dinucleotide, generating pyruvic acid and L-glutamic acid from L-alanine and 2-oxoglutaric acid as substrates by alanine aminotransferase, converting pyruvic acid and reduced nicotinamide adenine dinucleotide to lactic acid and oxidized nicotinamide adenine dinucleotide by lactate dehydrogenase, and measuring a decreased amount of reduced nicotinamide adenine dinucleotide or an increased amount of oxidized nicotinamide adenine dinucleotide, the improvement comprising bringing the sample into contact with L-alanine, 2-oxoglutaric acid, lactate dehydrogenase, and reduced nicotinamide adenine dinucleotide in the presence of a substance having an activity of inhibiting a lactate dehydrogenase activity, said substance being selected from the group consisting of oxamic acid, oxalic acid, oxalacetic acid, pyruvic acid, phosphoenolpyruvic acid, sodium dodecyl sulfate, lactic acid, and hydroxyglutaric acid, and salts thereof, and the concentration of said substance in the measuring system being a concentration exhibiting the lactate dehydrogenase activity which does not affect the measurement of the alanine aminotransferase activity.

2. The method according to claim 1, wherein the substance having an activity of inhibiting a lactate dehydrogenase activity is oxamic acid or a salt thereof.

3. The method according to claim 2, wherein a concentration of oxamic acid or a salt thereof is 0.005 to 5 mmol/L as a final concentration in the measuring system.

4. The method for measuring an alanine aminotransferase activity according to claim 1, wherein a concentration of lactate dehydrogenase is 100 U/L or more as a final concentration in the measuring system.

* * * * *